United States Patent [19]

Shu-Ti Lee et al.

[11] Patent Number: 4,684,805
[45] Date of Patent: Aug. 4, 1987

[54] METHOD AND APPARATUS FOR MEASURING STABLE ISOTOPES

[75] Inventors: Peter Shu-Ti Lee, Troy; Richard F. Majkowski, Southfield; Dale L. Partin, Sterling Heights, all of Mich.

[73] Assignee: General Motors Corporation, Detroit, Mich.

[21] Appl. No.: 767,742

[22] Filed: Aug. 21, 1985

[51] Int. Cl.⁴ ............................................. G01J 1/00
[52] U.S. Cl. ............................... 250/343; 250/339; 250/345
[58] Field of Search ............... 250/339, 341, 344–345, 250/373, 343, 346; 356/434–435, 440, 320, 413

[56] References Cited

U.S. PATENT DOCUMENTS 3,743,426  7/1973  Steinberg .
3,916,195  10/1985  Burch et al. ..................... 250/345
3,995,960  12/1976  Fletcher et al. .................. 250/343
4,023,909  5/1977  Ross .
4,157,470  6/1979  Kotaka et al. ................... 250/345
4,180,732  1/1980  Fabinski et al. .................. 250/345
4,281,248  7/1981  Fabinski et al. .................. 250/345
4,288,693  9/1981  Fabinski et al. .................. 250/345
4,500,207  2/1985  Maiden ............................. 250/343
4,519,710  5/1986  Luce et al. ........................ 250/343

OTHER PUBLICATIONS

"Monitor Trace Gases in Atmosphere" by Kumar Ramohalli, Nasa Tech Briefs, Summer 1985.

Primary Examiner—Craig E. Church
Assistant Examiner—John C. Freeman
Attorney, Agent, or Firm—Warren D. Hill

[57] ABSTRACT

Spectroscopic measurements of stable isotopes are performed using a tunable lead salt diode laser. The design of the system is based upon the optimization of isotopic spectral lines from two different path lengths in an absorption cell using a single gaseous sample. A short path cell to measure the more abundant species and a long path cell to measure the less abundant species are used. A micrometer adjustment of a path length is used for equalizing spectral line intensities to obtain a measure of isotope enrichment or of absolute isotopic concentration.

8 Claims, 6 Drawing Figures

METHOD AND APPARATUS FOR MEASURING STABLE ISOTOPES

FIELD OF THE INVENTION

This invention relates to a method for measuring stable isotopes and to apparatus for carrying out the method, and more particularly to the use of absorption spectroscopy for that purpose.

BACKGROUND OF THE INVENTION

It is very useful scientific investigations and in clinical evaluations to determine with a high degree of accuracy the concentration or relative concentrations of isotopes. For example, by substituting a tracer isotope for a naturally occurring isotope in a molecule the effect of subsequent processes on the molecule can be investigated. Such studies require precise measurements of isotopes.

The predominant method of isotope measurement had used radioactive isotopes. The drawbacks of that method include a limitation on the isotopes available for used, the effects of radioactivity on subjects exposed to that material, and the problem of radioactive waste disposal.

A variety of conditions that can be examined with harmless stable isotopes suggest the great potential of the present invention to clinical applications. A few, but by no means complete, examples of clinical tests taken from literature to which the present invention can be applied are:

A. Fat malabsorption and the underlying cause (intestinal mucosa defects, bilary obstruction, liver disease, pancreatic enzyme deficiency)—monitoring expired $CO_2$ after oral administration of labeled fat and/or labeled free fatty acid.

B. Ileal Dysfunction—monitoring breath $CO_2$ following injection of labeled bile acid.

C. Small-intestine Bacterial Overgrowth—increased labeled $CO_2$ excretion following intake of labeled $^{13}C$-xylose indicates this condition.

D. Liver Dysfunction (cirrhosis) and Liver Cancer—test based on the conversion of labeled $^{13}C$-galactose to expired $CO_2$.

It is evident that stable isotopes could beneficially be used in place of radioactive isotopes if there were a suitable measurement method and apparatus for stable isotopes. Indeed the use of stable isotopes in biomedical as well as general scientific and engineering applications has been hindered by the lack of a direct, simple and inexpensive measuring method. The present isotope ratio mass spectrometry is lacking in, specificity, ease of operation and cost effectiveness.

To take advantage of the benefits of stable isotope analysis there is need for a simple inexpensive portable clinical system that can be used for routine diagnosis. Such a system would for the first time enable most hospitals to perform stable isotopic tracer analysis.

SUMMARY OF THE INVENTION

It is therefore an object of the invention to provide a simple, accurate and inexpensive method and apparatus for measuring, especially stable isotopes.

The method of the invention is carried out by measuring vastly different concentrations of stable isotopes in a sample comprising the steps of; transmitting monochromatic radiation through the sample in at least two different path lengths and sweeping the radiation frequency over absorption lines of the isotopic molecules being measured, detecting the intensities of spectral lines in the different paths to measure more abundant isotopes in short path lengths and less abundant isotopes in long path lengths, and determining the concentrations of the isotopes from the path lengths and the measured spectral line intensities.

The apparatus of the invention is carried out by means for measuring vastly different concentrations of stable isotopes in a gaseous sample comprising; a tunable source of monochromatic radiation for scanning radiation through a frequency band, a sample cell arrangement having at least two optical paths through the same sample, the paths having different lengths in a ratio generally corresponding to the inverse ratio of the isotope concentrations, means for transmitting radiation from the source through the paths, detector means for measuring the spectral line intensity of each isotope, and circuitry responsive to the detector means for indicating relative line intensities.

BRIEF DESCRIPTION OF THE DRAWINGS

The above and other advantages of the invention will become more apparent from the following description taken in conjunction with the accompanying drawings wherein like reference numerals refer to like parts and wherein.

DESCRIPTION OF THE PREFERRED EMBODIMENT

This invention is directed to an infrared diode laser spectroscopy system to study isotopic compositions. Because of its frequency tunability, extremely narrow line width and high spectral power density, the system shows great promise of superseding the present isotope ratio mass spectrometry in accuracy, sensitivity, specificity, ease of operation and cost effectiveness. We emphasize here the biomedical applications and have demonstrated the method with isotopic compositions of CO, e.g., $^{12}C^{16}O$, $^{13}C^{16}O$, $^{12}C^{17}O$, $^{12}C^{18}O$. The method also has wider and other potentially useful applications in engineering and industry.

When an atom of a molecule is substituted with an isotope of the same element, the potential function and the configuration of the molecule is virtually unchanged. The vibration-rotation frequencies, however, are shifted due to isotopic substitution. These frequency shifts, form the basis of the present invention. As an example, the method for the determination of stable oxygen-18 tracer in biological tissues following intake of oxygen-18 labeled ozone ($^{18}O_3$) or nitrogen dioxide ($N^{18}O_2$) is explained in the following description. In the actual method, the tissue is processed and the isotopic composition in the resultant product, CO, is examined. Usually the most abundant isotope is present in much higher concentrations than the substituted isotope. This invention allows the accurate measurement of each and affords a direct comparison to furnish absolute values or enrichment values.

Figure 1:
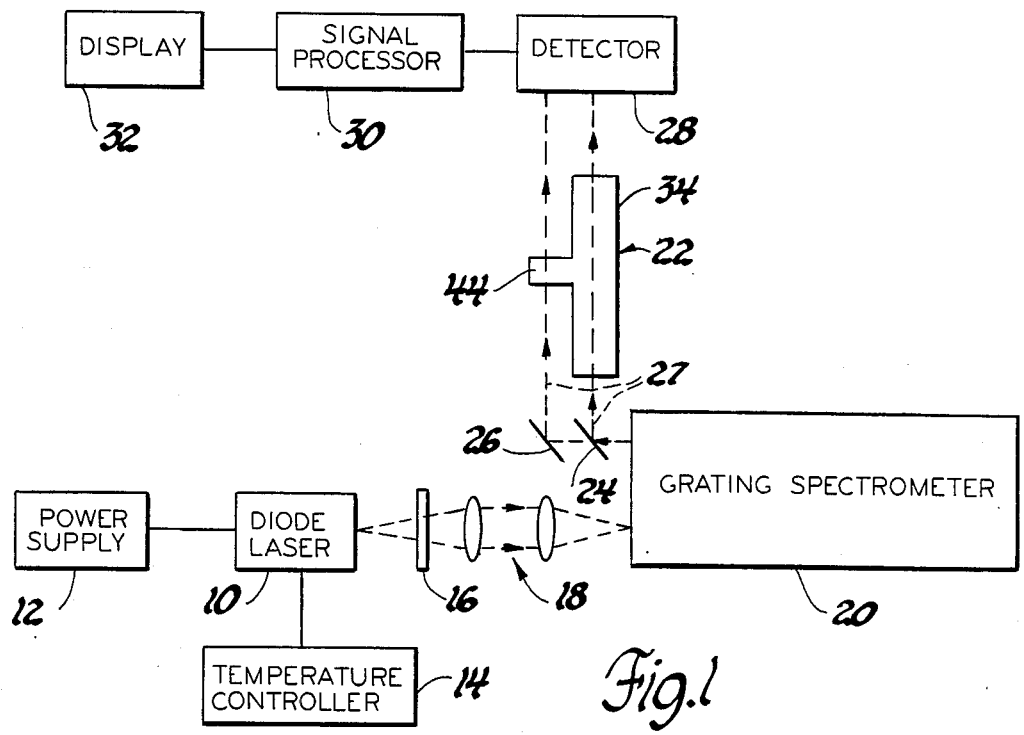
FIG. 1 is a block diagram of the apparatus according to the invention.

The apparatus as shown in FIG. 1 includes a tunable diode laser 10, a powder supply 12 for the laser 10, and a temperature controller 14. The laser is preferably of the lead salt type described in the U.S. Pat. Nos. 4,350,990 and 4,186,355 to Lo and the U.S. patent applications of Partin Ser. No. 565,397, filed Dec. 27, 1983 and Ser. No. 543,368, filed Oct. 19, 1983. Such lasers are tuned by varying the operating temperature and are available for operation in the wavelength range of 25 to 30, microns. The laser can be scanned over a small band, say about 0.5 to 3 cm$^{-1}$, at a rate of 500 cycles per second. By varying the injection current operating parameters of the laser system can be adjusted for a variety of isotopes and molecules. Any infrared active molecule can be studied by this system. The system therefore would be versatile rather than dedicated to a single isotopic species. The isotopic spectral lines are well resolved, thus eliminating any background interference that may be present in conventional mass spectrometry. The optical paths can be tailored to avoid processing of signals of vastly different intensity, thus greatly improving the accuracy of isotopic measurements.

Laser radiation passes through a chopper 16 and a lens system 18 to a grating spectrometer 20 which passes a single optical mode. The laser is tuned so that this mode spans the absorption lines of the desired isotopic molecules. The radiation then passes through a cell 22 containing the sample gas. A beam splitter 24 and a mirror 26 divide the radiation into at least two beams 27 and direct them through the cell 22 in separate paths. A detector or detectors 28 sense the radiation which passes the cell 22 and a signal processor 30 manipulates the detector signals and provides an output on display 32.

Figure 2:
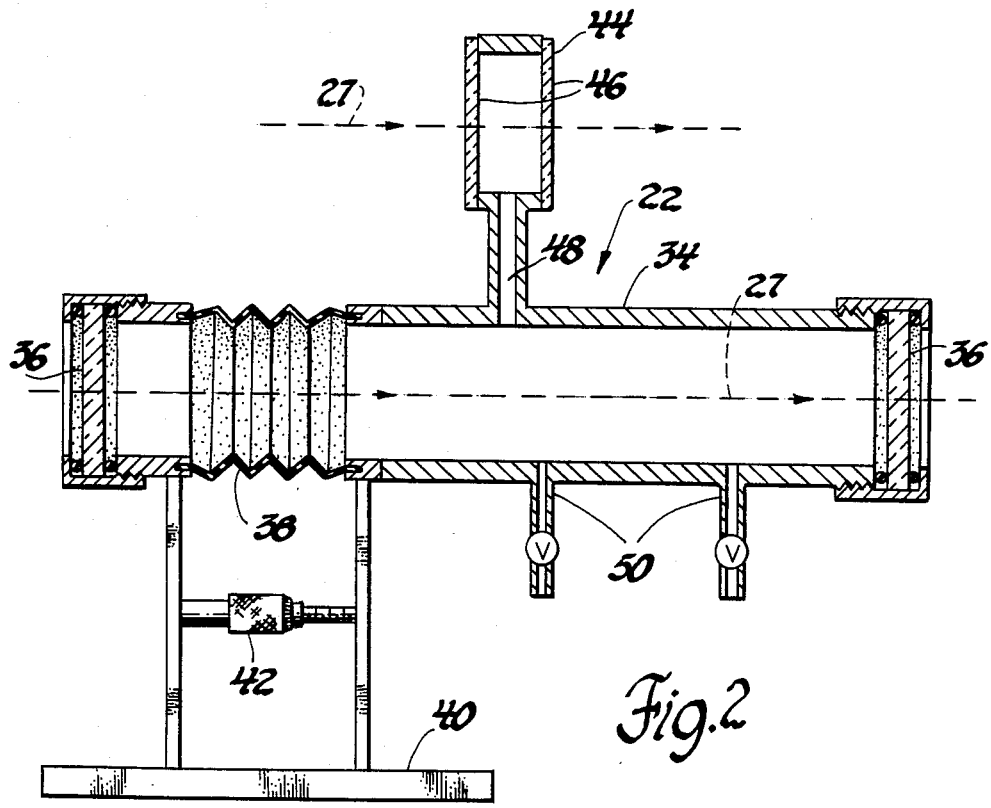
FIG. 2 is a schematic diagram of an absorption cell according to the invention for use in the apparatus of FIG. 1.

As best shown in FIG. 2 the optical absorption cell 22 has two path lengths (or more) of different lengths but both containing the same gas for analysis. A long chamber 34 has windows 36 at its ends and a flexible bellows 38 which allows longitudinal adjustment of the path length. The chamber 34 is mounted on a sliding base 40 and a micrometer adjustment 42 facilitates accurate measurement of any changes in the path length. A short chamber 44 with windows 46 is coupled to the long chamber 34 by a passage 48 which insures that both chambers contain the same gas. As generally indicated in FIG. 1, a laser beam 27 is directed through each chamber. A pair of ports 50 in the wall of the long chamber 34 provide inputs and outlets for sample gas.

Figure 3:
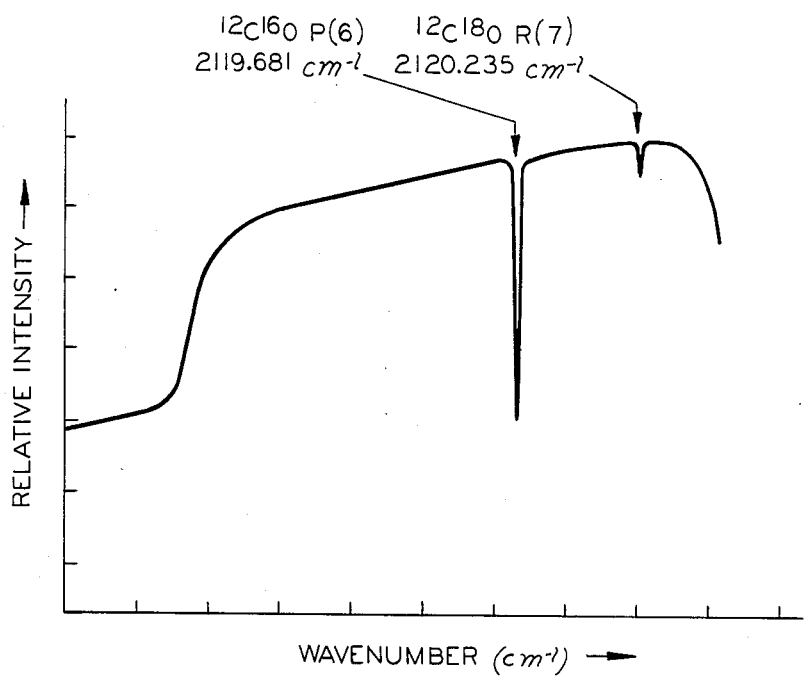
FIG. 3 is an oscilloscope trace of conventional absorption spectra.
Figure 4A:
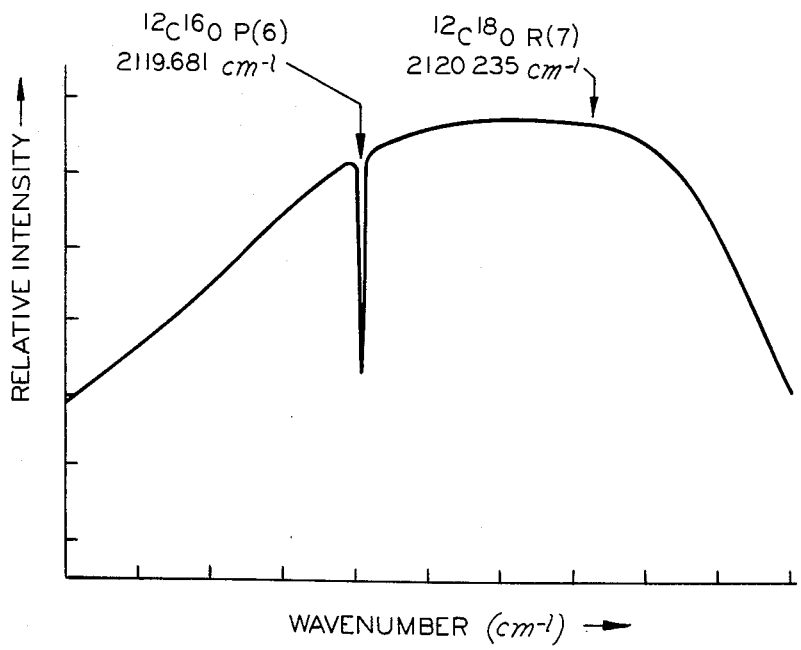
FIGS. 4a and 4b are oscilloscope traces of absorption spectra of stable isotopes made according to the invention.
Figure 4B:
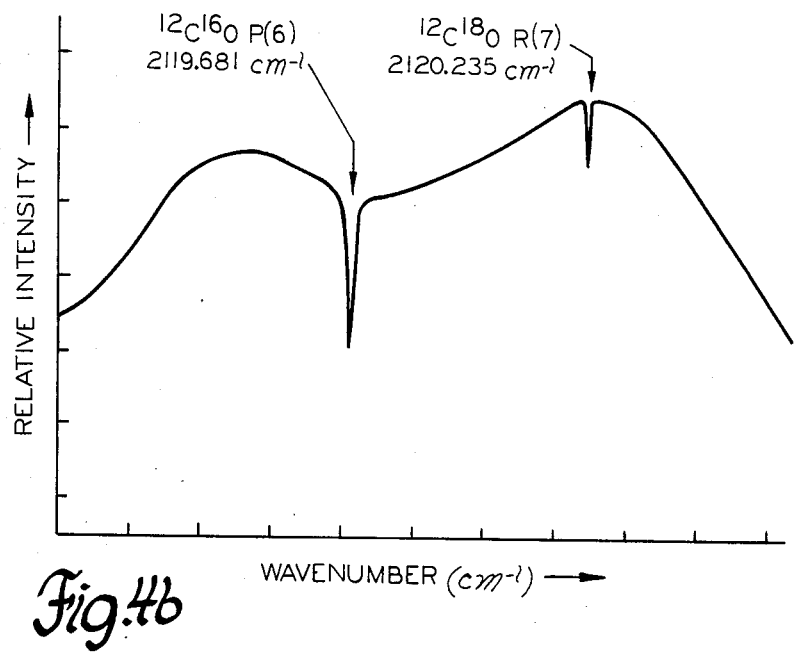

By providing absorption paths of greatly different lengths two isotopes of greatly different concentrations can be measured simultaneously. By selecting path lengths that are roughly in inverse ratio to the concentrations being measured comparable spectral line intensities can be achieved. FIG. 3 is an example of an oscilloscope trace of spectral lines absorbed by a a 2.6 torr sample of normal tank CO in a single absorbing path of 10 cm. The sample contains $^{12}C^{16}O$ and $^{12}C^{18}O$ in their natural abundance (500:1). The $^{12}C^{16}O$ P(6) line is completely saturated in this trace while the other line is barely visible. It is evident that such information is of limited usefulness for the measurement of absolute or relative concentrations. On the other hand, FIGS. 4a and 4b show the same two isotopic lines as shown in FIG. 3 using a short optical path length (3.5 mm) to obtain a non-saturated line for the more abundant isotope and a long path (40 cm) to obtain a good line for the less abundant isotope. The relative concentrations can be calculated from the measured line intensities and path lengths.

The signal from the two isotopes, although present in the sample in vastly different concentrations, can be equalized by carefully optimizing the optical absorption paths. A good signal to noise ratio for the least abundant isotope can thus be maintained to the same level as the most abundant isotope. This alleviates the problem associated with processing signals of vastly different intensity as encountered in isotope ratio mass spectrometry.

From the measured intensity, the isotopic abundance in the sample can be readily determined. The spectral absorption coefficient a (torr$^{-1}$ cm$^{-1}$) for the isotopic molecule is related to the incident laser intensity $I_o$ and the transmitted laser intensity $I$ by the Beer-Lambert law.

$$I = I_o e^{-apl}$$

where p is the partial pressure of the isotopic molecule (torr) and 1 is the path length (cm). Using calibration gas of known isotopic composition, a can be determined for the isotopic vibration-rotation lines. Since 1 is a constant, $I$ and $I_o$ can be experimentally measured, and the partial pressure of the isotopic molecule can be determined if the spectral absorption coefficient is known. The spectral absorption coefficient is a function of the line shape (Voigt profile) and the line strength. The line shape function has been tabulated and is greatly simplified by working at low pressure where the Doppler effect dominates. The line strength can be obtained either from the literature or from calibrated gas. The isotopic analysis of $^{12}C^{16}O$ and $^{12}C^{18}O$ is used as an example:

In a system with two optical path lengths, the transmitted laser intensities $I_1$ and $I_2$ for two isotopic spectral lines are:

$$I_1 = I_{10} e^{-a_1 p_1 l_1}$$

$$I_2 = I_{20} e^{-a_2 p_2 l_2}$$

where the index 1 refers to $^{12}C^{16}O$, and the index 2 refers to $^{12}C^{18}O$, and a, p and 1 have been previously defined.

The incident laser light intensity, $I_{10}$ and $I_{20}$ can be adjusted to be equal. From the natural abundance of oxygen isotopes, $p_1 = 489 p_2$, and from the relative intensities of P(6) and R(7) spectral lines, $a_1 = 0.831\ a_2$; thus for more abundant $^{12}C^{16}O$ with a path length of 1 mm, a path length of 406.4 mm is required for less abundant $^{12}C^{18}O$ to give an absorption signal of equal intensity. Thereafter, each 1 mm change of absorption path length from the $^{12}C^{18}O$ cell would correspond to an enrichment of 0.25% of $^{18}O$ from natural abundance (i.e. from 0.204% to 0.2045%). This is a rather significant and easily measurable change in path length. The subject system utilizes the precise micrometer measurement of change in path length to achieve equalization of spectral signals. It should be noted that the ratio of path lengths is generally or approximately equal to the inverse ratio of the isotope concentrations. That relationship is not exact because of the different absorption coefficients a.

Figure 5:
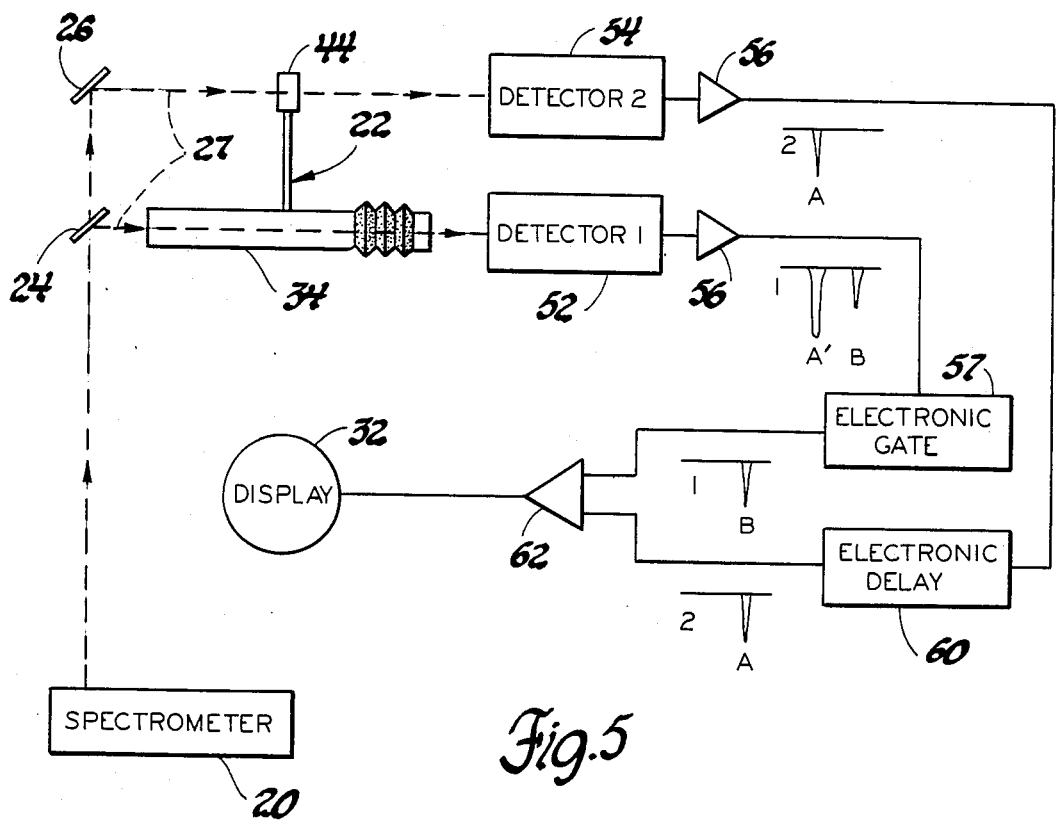
FIG. 5 is a diagram of the system according to the invention.

FIG. 5 illustrates the subject apparatus with a signal processing circuit for providing a null indication. Laser beams pass through the long and short chambers 34 and 44 of the absorption cell to detectors 52 and 54 respectively to product output signals representing the spectral line intensities. The signals are amplified by amplifiers 56 and are passed to an electronic gate 57 and an electronic delay circuit respectively. The outputs are then fed to inputs of a differential amplifier 62. The resulting difference signal is displayed on an oscilloscope or other display to indicate equality of spectral line intensities. The detector 52 receives a saturated signal A' corresponding to the most abundant isotope which is blocked by the gate 57. At the same time the detector 54 yields a signal A corresponding to the same isotope but not saturated. That signal A is delayed for comparison with signal B from detector 52 which corresponds to the less abundant isotope and which is passed by the gate 57.

In operation of the apparatus of FIG. 5 minor adjustments are made to the detector gain to equalize the two detector outputs while no gas is present in the cell. Then isotope enrichment measurements can be made in this manner. A reference gas is introduced into the sample cell and the cell length is adjusted by the micrometer adjustment 42 until the signals A and B are equal as shown by a zero output on the display 32. Then the sample gas is introduced into the cell 22 and again a micrometer adjustment is made to equalize the signals A and B. The change in micrometer setting represents the isotopic enrichment. The precise value of the enrichment is readily calculated as illustrated above and indeed may be computed electronically if the micrometer adjustment were automated to output an adjustment value. If the absolute isotropic ratio of a sample gas is desired the reference gas is not used and the micrometer setting required to equalize the two signals from the sample gas is used in conjunction with the Beer-Lambert Law to obtain the isotope ratio.

While the preferred embodiment of the invention uses two absorption path lengths to make measurements of two isotopes it should be apparent that the method and apparatus can be extended to the simultaneous measurements of more than two isotopes. It should also be apparent that while the chief advantage of the invention is that measurements are made with stable isotopes, it could also be used with radioactive isotopes, if desired.

The method and apparatus according to the present invention affords an accurate, compact, inexpensive, specific, versatile and easily maintainable system for isotopic measurement. As a result of this invention stable isotopic tracer measurements and potential clinical applications are made possible on a routine basis for the first time.

The embodiments of the invention in which an exclusive property or privilege is claimed are defined as follows.

1. The method of measuring different concentrations of isotopes in a sample comprising the steps of;
    transmitting monochromatic radiation through the sample in at least two different path lengths, which comprise at least one short path length and at least one long path length, and sweeping the radiation frequency over absorption lines of the isotopes being measured,
    detecting the intensities of spectral lines in the different paths to measure more abundant isotopes in the short path lengths and less abundant isotopes in the long path lengths,
    adjusting the relative path lengths to obtain a non-saturated spectral line intensity for each isotope being measured, measuring the relative path lengths, and determining the concentrations of the isotopes from the relative path lengths and the detected spectral line intensities.

2. The method of measuring different concentrations of stable isotopes in a gaseous sample comprising the steps of;
    transmitting monochromatic radiation through the sample in at least two different path lengths, which comprise at least one short path length and at least one long path length, and
    sweeping the radiation frequency over absorption lines of the isotopes being measured,
    detecting the intensities of spectral lines in the different paths to measure more abundant isotopes in the short path lengths and less abundant isotopes in the long path lengths,
    adjusting at least one path length to equalize the detected intensities, measuring the relative path lengths, and
    determining the concentrations of the isotopes from the relative path lengths and/or the detected spectral line intensities.

3. The method of measuring different concentrations of stable isotopes in a gaseous sample comprising the steps of;
    introducing a reference gas into a cell,
    transmitting monochromatic radiation through the reference gas in at least two different path lengths, which comprise at least one short path length and at least one long path length, and sweeping the radiation frequency over absorption lines of the isotopes being measured,
    detecting the intensities of spectral lines in the different paths to measure more abundant isotopes in the short path lengths and less abundant isotopes in the long path lengths,
    equalizing the detected intensities, removing the reference gas from the cell introducing the sample gas into the cell,
    repeating the transmitting and detecting steps, and
    adjusting the length of at least one of the paths to equalize the detected intensities for the sample gas, so that the amount of the adjustment represents the isotope enrichment in the sample.

4. Apparatus for measuring different concentrations of stable isotopes in a gaseous sample comprising;
    a tunable source of monochromatic radiation for scanning radiation through a frequency band,
    a sample cell arrangement having at least two optical paths through the same sample, the paths having different lengths in a ratio generally corresponding to the inverse ratio of the isotope concentrations,
    means for transmitting radiation from the source through the paths,
    detector means for sensing the spectral line intensity of each of isotope,
    means for adjusting at least one path length by measured amounts to adjust the line intensity of the corresponding path, and
    circuitry responsive to the detector means for determining isotope concentration from the path lengths and/or the respective line intensities.

5. Apparatus for measuring isotope enrichment in different concentrations of stable isotopes in a gaseous sample comprising;
    a tunable source of monochromatic radiation for scanning the frequency through a band, a sample cell arrangement having at least two optical paths through the same sample, the paths having different lengths in a ratio generally corresponding to the inverse ratio of the isotope concentrations, means for transmitting radiation from the source through the paths, detector means for measuring the spectral line intensity of an isotope in each optical path, and means for adjusting the relative path lengths by measured amounts to equalize the measured line intensities, so that the amount of adjustment for a sample gas relative to a reference gas is a measure of isotope enrichment.

6. Apparatus for measuring different concentrations of stable isotopes in a gaseous sample comprising;

a tunable source of monochromatic radiation for scanning radiation through a frequency band, a sample cell arrangement having at least two optical paths through the same sample, the paths having different lengths in ratio generally corresponding to the inverse ratio of the isotope concentrations, means for transmitting radiation from the source through the paths, detector means for measuring the spectral line intensity of each isotope, means for adjusting at least one of the path lengths for equalizing the line intensities, and circuitry responsive to the detector means for comparing the line intensities for indicating equality of line intensities for different path lengths.

7. Apparatus for measuring different concentrations of stable isotopes in a gaseous sample comprising:

a tunable source of monochromatic radiation for scanning radiation through a frequency band, a sample cell arrangement having at least two optical paths through the same sample, the paths having different lengths in a ratio generally corresponding to the inverse ratio of the isotope concentrations, means for transmitting radiation from the source through the paths, detector means for measuring the spectral line intensity of each isotope, and micrometer adjustment means for precisely adjusting at least one of the path lengths for varying the line intensities, so that isotope concentrations can be accurately determined from measured path lengths and line intensities.

8. The method of measuring the isotopic ratio of different concentrations of stable isotopes in a gaseous sample comprising the steps of;

transmitting monochromatic radiation through at least two different length paths in the absence of gas, detecting the transmitted radiation in each path and electronically equalizing the detectected signals, admitting sample gas into the paths, transmitting the radiation through the paths and sweeping the radiation frequency over absorption lines of the isotopes being measured, detecting the intensities of spectral lines in the different paths to measure more abundant isotopes in short path lengths and less abundant isotopes in long path lengths, adjusting at least one path length to equalize the detected intensities, measuring the relative path lengths and calculating the absolute isotopic ratio from the relative path lengths, the absorption coefficients and the Beer-Lambert law.

* * * * *

UNITED STATES PATENT AND TRADEMARK OFFICE
CERTIFICATE OF CORRECTION

PATENT NO. : 4,684,805

DATED : August 4, 1987

INVENTOR(S) : Peter S. Lee; Richard F. Majkowski & Dale L. Partin

It is certified that error appears in the above-identified patent and that said Letters Patent is hereby corrected as shown below:

```
Column 1, line 20, delete "had" and substitute -- has --;
         line 32, delete "bilary" and substitute -- biliary --.
Column 3, line  5, delete "powder" and substitute -- power --;
         line 12, delete "25" and substitute -- 2.5 --;
         line 13, delete the comma after "30";
         line 15, delete the period after "second";
         line 15, delete "By" and substitute -- by --;
         line 15, insert a period after "current";
         line 15, delete "operating" and substitute
                  -- Operating --.
Column 5, line  1, delete "product" and substitute -- produce --.
```

Signed and Sealed this

Second Day of February, 1988

Attest:

DONALD J. QUIGG

Attesting Officer

Commissioner of Patents and Trademarks